United States Patent
Nguyen et al.

(10) Patent No.: US 9,921,228 B2
(45) Date of Patent: Mar. 20, 2018

(54) ELECTRONIC LATERAL FLOW TEST ARRANGEMENT AND METHOD

(71) Applicant: NXP B.V., Eindhoven (NL)

(72) Inventors: Viet Nguyen, Leuven (BE); Franciscus Petrus Widdershoven, Eindhoven (NL); Roel Daamen, Herkenbosch (NL)

(73) Assignee: NXP B.V., Eindhoven (NL)

( * ) Notice: Subject to any disclaimer, the term of this patent is extended or adjusted under 35 U.S.C. 154(b) by 117 days.

(21) Appl. No.: 14/363,449

(22) PCT Filed: Dec. 6, 2012

(86) PCT No.: PCT/EP2012/074624
§ 371 (c)(1),
(2) Date: Jun. 6, 2014

(87) PCT Pub. No.: WO2013/083686
PCT Pub. Date: Jun. 13, 2013

(65) Prior Publication Data
US 2014/0323350 A1    Oct. 30, 2014

(30) Foreign Application Priority Data

Dec. 7, 2011 (EP) .................................... 11192423

(51) Int. Cl.
*G01N 33/50* (2006.01)
*G01N 33/68* (2006.01)
(Continued)

(52) U.S. Cl.
CPC ....... *G01N 33/689* (2013.01); *G01N 27/3274* (2013.01); *G01N 33/5438* (2013.01); *G01N 33/558* (2013.01)

(58) Field of Classification Search
None
See application file for complete search history.

(56) References Cited

U.S. PATENT DOCUMENTS 4,822,566 A * 4/1989 Newman ............ G01N 33/5438
324/687
5,580,794 A * 12/1996 Allen .................... B01L 3/5023
422/404
(Continued)

FOREIGN PATENT DOCUMENTS

CN     1791796 A     6/2006
EP     2508874 A1    10/2012
(Continued)

OTHER PUBLICATIONS

International Search Report for application No. PCT/EP2012/074624 (dated Jan. 25, 2013).
(Continued)

*Primary Examiner* — Erik B Crawford

(57) ABSTRACT

A lateral test flow arrangement for a test molecule is disclosed, comprising: a test strip for transporting an analyte away from a sampling region and towards an absorbing region, the test strip having therein and remote from the sampling region, a test region for functionalization with a molecule which binds to the test molecule or to a conjugate of the test molecule; a sensing test capacitor having electrodes extending across the test strip at least partially aligned with the test region and being physically isolated therefrom; a reference test capacitor having electrodes extending across the test strip and being physically isolated therefrom; and an electronic circuit configured to measure a time-dependant capacitance difference between the sensing test capacitor and the reference test capacitor. A method for carrying out that lateral flow tests is also disclosed, as are test systems and in particular pregnancy test systems.

15 Claims, 5 Drawing Sheets

(51) Int. Cl.
*G01N 33/558* (2006.01)
*G01N 33/543* (2006.01)
*G01N 27/327* (2006.01)

(56) References Cited

U.S. PATENT DOCUMENTS

| | | | |
|---|---|---|---|
| 5,958,791 A * | 9/1999 | Roberts | C12Q 1/6816 204/288 |
| 6,194,224 B1 * | 2/2001 | Good | G01N 33/558 422/423 |
| 6,358,752 B1 * | 3/2002 | Durst | G01N 33/558 204/194 |
| 6,485,983 B1 * | 11/2002 | Lu | G01N 33/558 204/288 |
| 7,834,646 B2 | 11/2010 | Chambon et al. | |
| 2003/0098233 A1 * | 5/2003 | Kermani | G01N 27/3274 204/400 |
| 2003/0180815 A1 * | 9/2003 | Rawson | G01N 33/558 435/7.9 |
| 2005/0239216 A1 | 10/2005 | Feistel | |
| 2006/0281193 A1 * | 12/2006 | Petrilla | G01N 33/558 436/514 |
| 2010/0062414 A1 * | 3/2010 | Yamamoto | B01L 3/502738 435/4 |
| 2010/0274181 A1 * | 10/2010 | Wang | A61M 5/1723 604/66 |
| 2011/0053289 A1 * | 3/2011 | Lowe | B01L 3/5027 436/501 |
| 2011/0186428 A1 * | 8/2011 | Beaty | G01N 27/327 204/403.01 |
| 2011/0208435 A1 | 8/2011 | Elder et al. | |
| 2012/0073986 A1 * | 3/2012 | Jackson | G01N 33/5438 205/775 |

FOREIGN PATENT DOCUMENTS

| | | |
|---|---|---|
| JP | 2010286261 A | 12/2010 |
| WO | 02/10754 A2 | 2/2002 |
| WO | 2004/010143 A2 | 1/2004 |
| WO | 2006/010072 A2 | 1/2006 |
| WO | 2008/040983 A1 | 4/2008 |
| WO | 2009/144507 A1 | 12/2009 |

OTHER PUBLICATIONS

Office action from counterpart application CN 201280060417.6 (dated Feb. 9, 2015).

U.S. Appl. No. 14/845,166; 38 pages (filed Sep. 3, 2015).

Extended European Search Report for Patent Appln. No. 16183667.1 (dated Dec. 5, 2016) 7 pages.

Notice of Allowance U.S. Appl. No. 14/845,166, 12 pages (dated Jun. 29, 2017).

* cited by examiner

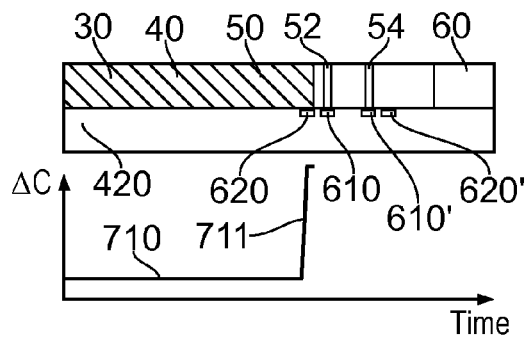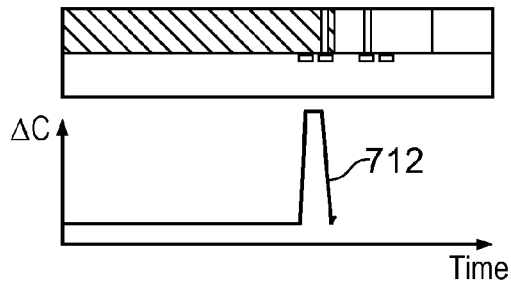
FIG. 7(a)  FIG. 7(b)
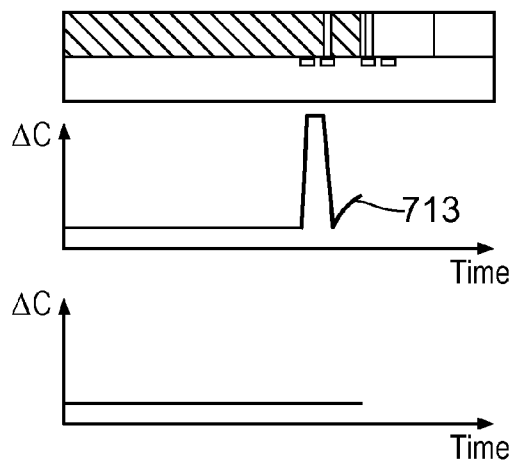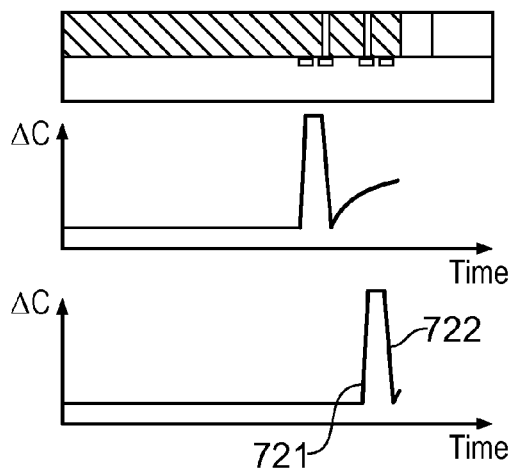
FIG. 7(c)  FIG. 7(d)
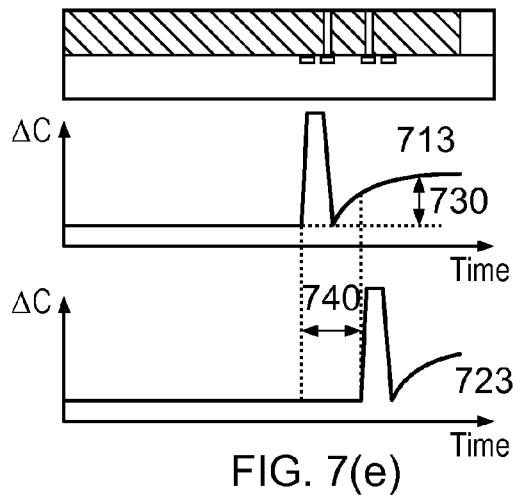
FIG. 7(e)

ELECTRONIC LATERAL FLOW TEST ARRANGEMENT AND METHOD

FIELD OF THE INVENTION

This invention relates to lateral flow test arrangements and to methods of carrying out lateral flow tests. It also relates to test systems, such as for example pregnancy test systems.

BACKGROUND OF THE INVENTION

A conventional lateral flow test apparatus comprises an elongate membrane along which a sample analyte flows. The sample analyte may or may not contain a test molecule at a concentration level of interest. Typically, at a specific test region, the membrane is impregnated with molecules which are chosen because they interact either with the test molecule, or with a marker molecule which may be conjugated with the test molecule. The impregnated molecules are typically bioreceptors. The presence of the test molecule in the sample analyte, at or above the concentration level of interest, results in an accumulation of the markup at the test line. Provided the marker is optically active, once a sufficiently high concentration of markers has accumulated at the test line, this may be observed by the user of the test apparatus. The test region is typically defined as a test line which extends across the membrane, but does not extend significantly along it, so may have dimensions of: the membrane width (across the membrane)×0.5-1.5 mm and typically 1 mm (along the membrane).

In order to avoid false-negative results (or in some instances false positive, as will be discussed below in relation to competitive assays results), lateral flow tests generally include a control line at which marker molecules may also accumulate. The presence of a visual change at the control line provides confirmation of adequate flow along the lateral flow test apparatus.

In order to reduce the inherent subjectivity of a visual inspection by the user, it has been proposed to replace the visual inspection by an integrated optical system. Such an optical lateral flow test system which uses LEDs as a light source and photodiodes as an optical measuring device is disclosed in international patent application Publication WO2009/144507-A1.

International patent application Publication WO02/10754 discloses an assay apparatus comprising a means of providing quantitative measurement of an analyte in which a meter determines, with polymer coated electrodes, the increase in capacitance of a region of a test strip, wherein the change in capacitance is directly related to the quantity of bound labelled target analyte, and thus to the quantity of target analyte in a patient sample.

SUMMARY OF THE INVENTION

According to a first aspect there is provided lateral flow test arrangement for a test molecule and comprising: a test strip for transporting an analyte from a sampling region towards an absorbing region, the test strip having thereacross and remote from the sampling region, a test line for functionalization with a molecule which binds to the test molecule or to a conjugate of the test molecule; a sensing test capacitor having electrodes extending across the test strip at least partially aligned with the test region; a reference test capacitor having electrodes extending across the test strip; and an electronic circuit configured to measure a time-dependant capacitance difference between the sensing test capacitor and the reference test capacitor. The test region may be a test line which extends across the test strip, and the electrodes of the test capacitor may be longitudinally aligned with the test line and extend at least partially across the test strip. It will be appreciated that, in use, the electrodes will not be in direct electrical contact with fluid being transported through the test strip, but there will be electrical insulation therebetween. This may arranged, for instance by physically isolating the electrodes from the test strip, for example by forming the electrodes on the side of a flex-foil remote from the strip or embedding the electrodes between layers of a flexfoil. In the non-limiting latter case, electrodes, with their electrically insulating flexfoil sleeving, may be embedded at least partially within the test strip.

In embodiments, at least one of: the electrodes of the sensing test capacitor are both on the same side of the strip, and the electrodes of the reference test capacitor are both on the same side of the strip. Thus the electrodes may be formed on or in a flexfoil which may act as a backing sheet or substrate to the test strip. This may be for either the sensing test capacitor or the reference test capacitor or both. This is a particularly simple arrangement. In other embodiments, the electrodes of a capacitor may be one on either side of the test strip. Accumulation of marker molecules in the test region then may alter the permittivity of the material directly between the electrodes—that is to say, the capacitor conductive plates—and cause a relatively larger change to the capacitance, compared with the arrangement where both electrodes are on the same side of the strip, although the physical layout, to provide the electrodes on opposite sides of the test strip may be more complex.

In embodiments, the electrodes of the sensing test capacitor and the electrodes of the reference test capacitor comprise tracks in a flex-foil, and the flex-foil is arranged to provide electrical isolation between the electrodes and the strip.

In embodiments, the electronic circuit is further configured to measure the capacitance of at least one of the sensing test capacitor and the reference test capacitor at a plurality of frequencies. By measuring at different frequencies, and in particular by sweeping the frequency across a suitable frequency range, a frequency may be determined at which the signal-to-noise ratio of the capacitance measurement is optimum.

In embodiments, the test strip further comprises a control region for functionalization with a different molecule, and the lateral flow test arrangement further comprises: a sensing control capacitor having electrodes extending across the test strip at least partially aligned with the control region and extending across the test strip; and a reference control capacitor having electrodes extending across the test strip; wherein the electronic circuit is further configured to measure a time-dependant capacitance difference between the sensing control capacitor and the reference control capacitor. The electrodes which extend across the strip may extend across the whole of the width of the test strip, or may extend only a part of the way across the width; they may also extend beyond the edge of the test strip.

In embodiments, the electronic circuit is further configured to determine a volume flow rate from the time-dependant capacitance difference between the sensing control capacitor and the reference control capacitor, and the time-dependant capacitance difference between the sensing test capacitor and the reference test capacitor.

In embodiments, the test strip comprises a membrane with a porosity between 66% and 84% by volume. This is typical for readily available nitrocellulose membrane; however, other membranes with a porosity of up to, or even over, 96% may also be used. A high porosity allows for a high volume flow rate laterally along the test strip, since there is little impedance to flow.

In embodiments, the lateral flow test arrangement further comprises a data display for displaying data from the electronic circuit. The apparatus may thus be self-contained and directly read by a user; in embodiments, the lateral flow test arrangement further comprises a communication circuit for communicating data from the electronic circuit to an external device. Communication may be wired or wireless, and may be by a proprietary format or according to a known standardised communication protocol. Then, the data may be read by the user; further data processing may be applied; the data may be further transmitted to a data aggregator or to, for instance, a health professional for further analysis or diagnosis; or the data may be directly archived into a patient's medical records. Combinations of the above may also be applicable, for instance without limitation, a read-out on the unit may be combined with communication from the electronic circuit to an external device and thence to a computer of a medical professional for further analysis and/or follow-up with the patient. The lateral flow test arrangement may further comprise a battery or other energy storage means. Such a battery may allow the lateral flow test arrangement to store data or test results for, for instance, later display, analysis, or transmission, whether wirelessly or wired. In the case of wireless transmission, power for the transmission—and even in embodiments for data processing—may be provided by the receiving device. The arrangement may include other functionality. For example and without limitation, the arrangement may include circuitry or means to date-stamp or time-stamp to indicate the moment of a test, and shelf-life indication to provide confirmation as to whether the test was carried out within an approved time-window. A unique or other identifier may be added to the test data, in order to personalise it or encrypt it or provide further security for the data. In other embodiments, functionality to measure or check environmental conditions such as temperature or humidity, which may have an impact on the test results, may be included.

According to another aspect there is provided a pregnancy test system comprising a lateral flow test arrangement as described hereinabove.

In embodiments, the test strip has thereacross and remote from the sampling region, a further test line for functionalization with a further molecule which binds to the further test molecule; and the lateral flow test further comprises a further sensing test capacitor having electrodes longitudinally aligned with the test line and extending across the test strip; a further reference test capacitor having electrodes extending across the test strip; wherein the electronic circuit is further configured to measure a time-dependant capacitance difference between the further sensing test capacitor and the further reference test capacitor. Thus a lateral test apparatus according to embodiments may be able to test for more than one type of test molecule. This is particularly useful in situations in which it is desired to screen for a plurality of different test molecules, or where no one single test molecule provides a strong indicator of, for instance, a specific medical condition, but the presence of each of several types of molecules, when considered in combination, provides a stronger indication. In conventional lateral flow test apparatus a plurality of apparatuses or a more complex testing configuration would be required, for instance requiring complex optical routing or multiple optoelectronic components. In embodiments, by replicating only a few features such as only a further test line, a pair of capacitors, and an additional input to the electronic circuit, the lateral flow test can become a multiplexed test or multiplexed assay, with limitation additional complexity or cost.

According to another aspect there is provided a test system for monitoring the concentration of a target molecule, or of a plurality of different target molecules, in a biological fluid, comprising a lateral flow test arrangement described above. The target molecule or molecules may be a respective one of or a plurality of molecules from the set consisting of DNA, proteins, enzymes, peptides, cells, bacteria, small molecules, and hormones.

According to yet another aspect, there is provided a method of using a lateral flow test arrangement comprising: a test strip having a sampling region towards an absorbing region, the test strip having thereacross and remote from the sampling region, a test line functionalized with a molecule which binds to a test molecule; a sensing test capacitor having electrodes longitudinally aligned with the test line and extending across the test strip; a reference test capacitor having electrodes extending across the test strip; and an electronic circuit; the method comprising: transporting the analyte from a sampling region towards an absorbing region; measuring a difference in capacitance between the sensing test capacitor and the reference test capacitor; and determining a concentration of the test molecule from the difference in capacitance.

In embodiments, the test strip further comprises a control line functionalized with a different molecule, and the lateral flow test arrangement further comprises: a sensing control capacitor having electrodes longitudinally aligned with the test line and extending across the test strip; and a reference control capacitor having electrodes extending across the test strip; and the method further comprises: measuring a difference in capacitance between the sensing control capacitor and the reference control capacitor; and determining a volume flow rate from the time-dependant difference in capacitance between the sensing control capacitor and the reference control capacitor, and the time-dependant difference in capacitance between the sensing test capacitor and the reference test capacitor.

As well be familiar to the skilled person, the testing process may include a labelling stage, in which the analyte is bound to an antibody with having a label thereon. The process may use any of different kinds of labels such as inorganic particles, including metals such as gold, silver, carbon and the like, oxides such as tantalum oxide, iron oxide, silicon oxide and the like and organic particles such as polystyrene and the like. The capacitive signal sensitivity will generally be dependent on the dielectric properties of the particles compared with the sample medium. The labelling stage may occur in the test device, by means of a conjugate pad, in which the conjugate may comprise the label, as will be described in more detail hereinbelow, or may occur prior to introduction of the analyte into the lateral flow test device.

These and other aspects of the invention will be apparent from, and elucidated with reference to, the embodiments described hereinafter.

BRIEF DESCRIPTION OF DRAWINGS

Embodiments of the invention will be described, by way of example only, with reference to the drawings, in which

FIG. 7 shows, at FIG. 7(a) to FIG. 7(e) respectively, delta-C for the test line and control line capacitors at different moments during a test.

Figure 1:
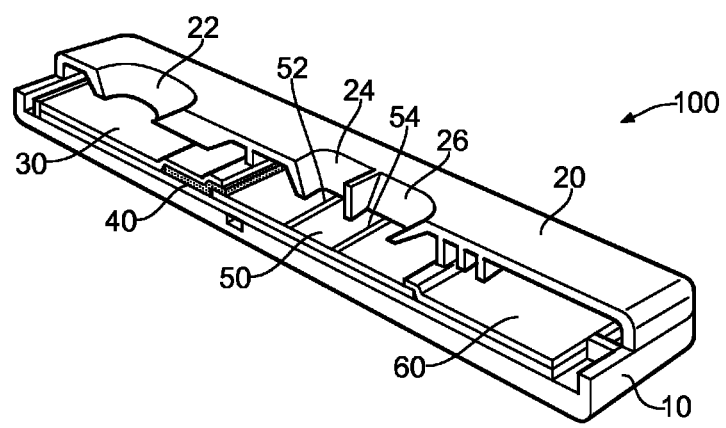
FIG. 1 shows a cutaway schematic of a conventional lateral flow test arrangement.

It should be noted that the Figures are diagrammatic and not drawn to scale. Relative dimensions and proportions of parts of these Figures have been shown exaggerated or reduced in size, for the sake of clarity and convenience in the drawings. The same reference signs are generally used to refer to corresponding or similar feature in modified and different embodiments.

DETAILED DESCRIPTION OF EMBODIMENTS

FIG. 1 shows a cutaway schematic of a conventional lateral flow test device 100. The device has a bottom housing 10, and a top housing 20 shown longitudinally cutaway. The top housing 20 has three ports therein. The first port 22, positioned towards one end of the arrangement, is a sample port, whereby a sample fluid such as urine may be introduced into the device. The other two ports 24 and 26 are positioned remote from the sample port 22, and are for viewing test results as will be described hereinbelow. Inside the device there is a sample pad 30 for receiving the sample introduced into the device through sample port 22. In contact with the sample pad 30 is a conjugate pad 40. The conjugate pad 40 is impregnated with conjugate molecules. In turn, the conjugate pad 40 is in contact with a test strip 50, which takes the form of a membrane. The test strip is an elongate strip which may typically be 5 mm or 3 mm in width and between 5 cm and 15 cm in length and extends generally along the device and enables, in use, a lateral flow, that is to say a flow along the device, of the sample. At the opposite end of the test strip from the sample port, the test strip is in contact with an absorbent pad 60. The absorbent pad 60 acts as a waste tank or reservoir to receive fluid which has flowed laterally along the test strip. Partway along the test strip, and underneath the ports 24 and 26 respectively are a test line 52 and a control line 54. Test line 52 and control line 54 are used to determine the results of the test, as will be described hereinbelow with reference to FIG. 3.

In the case of a lateral flow test device targeted for testing whether a specific molecule is present in urine, the physical form of the device is generally such as to be conveniently held by the user whilst passing urine. The requirement that the device may be conveniently handheld imposes minimum requirements on the thickness and width of the device: conversely, there may be competing requirements to minimise the bill of materials, which provides a downward pressure on the thickness and width of the device, and to provide sufficient volume in both the conjugate pad 40 and the test and control lines 52 and 54 to provide adequate sensitivity provides a lower limit on the dimensions.

The device shown in FIG. 1 is designed for visual inspection: that is to say the user inspects both the test line and control line at the end of the testing as will be described in more detail hereinbelow.

However, it is known that a visual inspection is a subjective matter, and it has been found that, in some circumstances, the results from as many as one in four tests are incorrectly read by the user.

Figure 2:
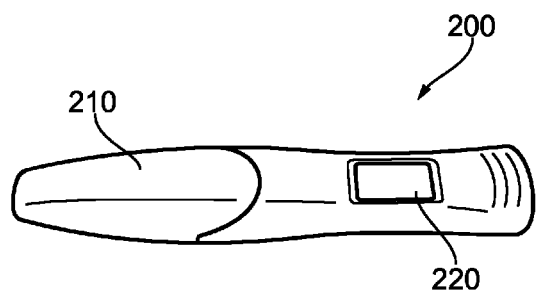
FIG. 2 shows an outline of the lateral flow test system having a digital readout.

In order to overcome this, there have been developed digital readouts of the test result. FIG. 2 shows an outline of the lateral flow test system 200 having a digital readout. The device shown in FIG. 2 is generally elongate similar to that shown in FIG. 1. The end of the device having the sample port is shown covered by a cap 210. Towards the other end of the device is shown a digital readout 220. In such a device, visual inspection of the colour contrast of the test line 52 and control line 54 is replaced by an optical detection system, comprising one or more light sources such as LEDs and one or more detectors such as photodiodes (not shown). Typically, the LEDs and photodiodes are located either side of the membrane 50, and light is shone from the LED through the membrane and received by the photodiode. The attenuation in the light which is attributable to opaqueness of the test and control lines, beyond that attributable to absorption by the membrane itself, may thus be taken as a measure of the opaqueness of the line. In an alternative arrangement, the LEDs and photodiode may be on the same side of the membrane, and the reduction in reflection from the surface due to accumulation of a marker molecules on the test (or control) lines, is measured.

Figure 3A:
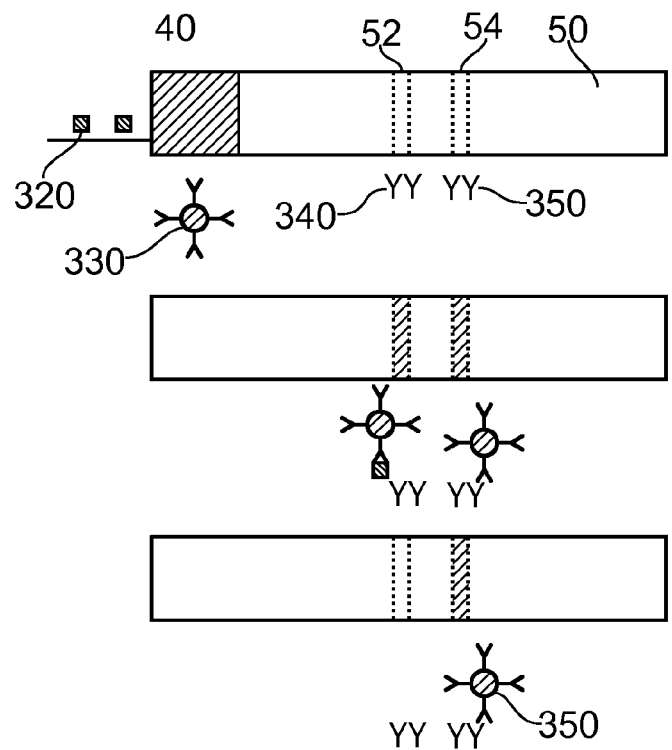
FIG. 3 shows schematics of, at FIG. 3(a) a direct immunoassay lateral flow test and at FIG. 3(b) a competitive immunoassay lateral flow test.
Figure 3B:
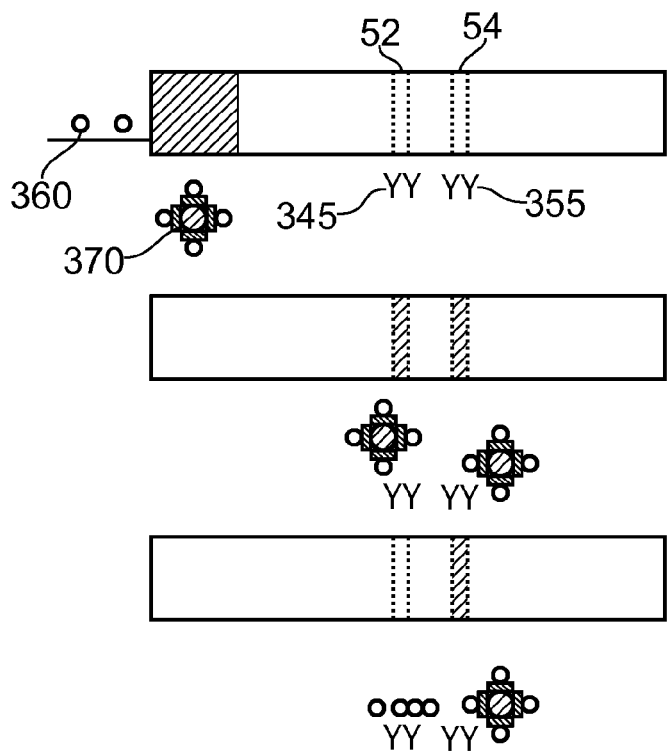

FIG. 3 shows schematics of, at FIG. 3(a) a direct immunoassay lateral flow test and at FIG. 3(b) a competitive immunoassay lateral flow test. It will be appreciated that embodiments are not limited to these types of lateral flow test, but can be used in other types of lateral flow test, such as without limitation replacement assays. FIG. 3(a) shows schematics of the reactions along the test strip at three moments during the test, for a direct immunoassay lateral flow test. In the top schematic, a sample analyte is introduced into the sample port. As shown, the analyte includes a certain concentration of a specific molecule 320—the test molecule. In the case of a lateral flow test for pregnancy, the molecule 320 may be a specific protein which is known to be present in the urine of a pregnant woman and not present in the urine of a woman who is not pregnant. The conjugate pad 40 is impregnated with a specific type of marker molecule 330. The marker molecule 330 is chosen such that it binds with the test molecule 320, and is optically active. Early marker molecules were organic markers, such as polystyrene beads. Currently used marker molecules typically include a nano particle of gold, since this has been found to be both optically active and stable over time. In addition to such colloidal gold labels, it is known to use colloidal carbon, and liposomes—although the latter have been found to have stability problems. It should be noted that the dimensions of the gold nano particle within the marker molecule 330 typically are of the order of 50 nm, and thus are significantly less than the wavelength of the light used to detect their presence, which in the case of a visual inspection is of course in the visible region. The optical effect is therefore not one of direct reflection or absorption but of interference with the electrical and magnetic fields of the light.

As shown in the top strip of FIG. 3(a), the test line and control lines 52 and 54 have been impregnated with bioreceptors 340 and 350 respectively. Turning now to the middle strip of FIG. 3(a), this shows the situation where the analyte includes target molecules 320. In this case, the presence of the analyte causes the marker molecules 330 to flow along the test strip 50. Some of the marker molecules 330 have conjugated with the test molecules 320 in the sample. The bioreceptor 340 is chosen to bind specifically to the conjugate of the test molecule 320 and the marker molecule 330. Since the bioreceptors 340 are fixed at the test line, the conjugated molecules therefore accumulate at this test line, and this may be observed by an increasing coloration of the line. By coloration, is meant here an increased contrast with the background colour of the membrane or strip. The membrane is typically white; also it typically has a certain level of translucence, which depends on its material and thickness: so accumulation of the conjugated molecules may also result in an increase in opaqueness. As is also shown in the middle strip of FIG. 3(a), unconjugated marker molecules 330 which have not bound to bioreceptor 340 (because of to the specificity of this bioreceptors) pass through this test line, and then bind to bioreceptor 350 which is not specific to the conjugate. The control line thus also turns opaque due to the presence of the (unconjugated) marker molecule 330. Turning now to the bottom strip of FIG. 3(a), this shows the case where there are no test molecules 320 present in the analyte. In this case, the marker molecules 330 do not conjugate with the test sample, and thus no marker molecules bind to the bioreceptor 340. However, the unconjugated marker molecules still bind to the non-specific biomolecules 350. So, at the end of the test in this case, the control line 54 has turned opaque whereas the test line 52 has not turned opaque.

Thus the presence of opaqueness on the test line 52 provides an indication that the test molecule 320 is present in the sample. Opaqueness in the control line 54 provides confirmation that the test has correctly operated: in the absence of opaqueness of this control line, it may be assumed that inadequate, or no, flow has taken place and consequently that the absence of opaqueness on test line 52 should not be taken as a negative result.

FIG. 3(b) shows schematics of the reactions along the test strip at three moments during the test, for a competitive immunoassay lateral flow test. This lateral flow test is similar to that shown in FIG. 3(a), in that a sample analyte is introduced, and the sample analyte may include test molecules 360. The sample flows across a conjugate pad containing conjugate molecules 370. In this case, however, the bioreceptors 345 at the test line preferentially bind to the test molecule 360, although they also will bind to conjugate molecule 370. Thus, if test molecule 360 is in the analyte, this binds to the bioreceptor 345 which, as a consequence does not turn the test line opaque since it there is no marker attached, whereas, if test molecule 360 is not present in the analyte, conjugate molecules 370 binds to the bioreceptor 345 which, as a consequence does turn the test line opaque, since the conjugate molecule does include an optical marker. Similar to the direct lateral flow test described above, a control line is included at which there is a further bioreceptor 355 which binds to the conjugate molecule 370—absence of an opacity at this line indicates that the test has not been properly completed and thus operates to limit or prevent false positive results.

Figure 4:
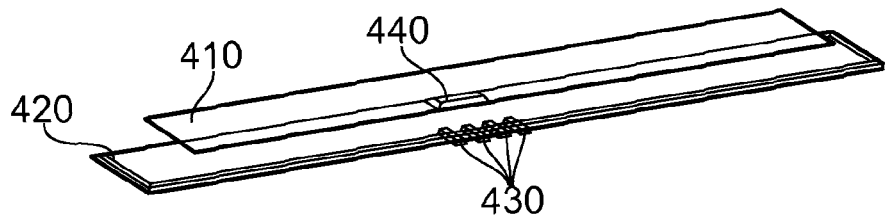
FIG. 4 shows an exploded view of part of the lateral flow test arrangement according to embodiments.

FIG. 4 shows an exploded view of part of a lateral flow test arrangement according to embodiments. The lateral flow test strip 410 itself is similar to that described above and thus details are not shown, for the sake of clarity. However, underneath the test strip 410 is a substrate 420, on the underside of which are capacitors 430. The electrodes from the capacitors 430 may be interdigitated, which is not visible in this diagram, but may be seen in more detail in FIG. 6 below. In embodiments, the substrate 420 may be a flex-foil such as will be familiar to the skilled person and is commonly used in electronic circuitry, and the electrodes of the capacitors 430 may be formed on the undersigned of the flexfoil as conductive tracks. The flexfoil may be made from polymeric material such as polyimide, polyether ether ketone, polyvinyl chloride, or transparent conductive polyester, and as is suggested by the name, may be flexible or even foldable. PEN, that is poly(ethylene naphthalate) is also known as a flex foil, as is PET, that is poly(ethylene terephthalate) which is used due to its low cost and relatively high temperature stability. Also attached to the underside of the flexfoil may be an integrated circuit 440. The integrated circuit 440 may include a capacitance measurement circuit in order to measure the capacitance of each of capacitors 430. The integrated circuit 440 may further include a differential capacitance measurement circuit capable of measuring the difference in capacitance between two capacitors, that is to say, the capacitance difference, as will be described in more detail below.

Figure 5:
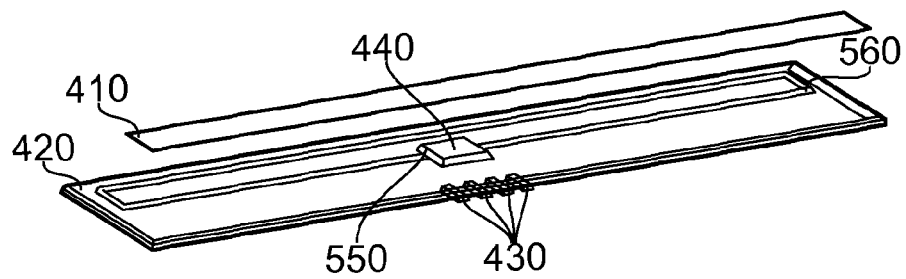
FIG. 5 shows an exploded view of part of the lateral flow test arrangement according to other embodiments.

FIG. 5 shows an exploded view of part of a lateral flow test arrangement according to other embodiments. The arrangement shown in this figure is generally similar to that shown in FIG. 4 and includes a lateral flow test strip 410, under which is a substrate for 420. On the underside of the substrate 420 are formed tracks in the form of electrodes pairs of electrodes to form capacitors 430. The capacitors 430 are connected to an integrated circuit 440. However in this embodiment, integrated circuit 440 further includes a circuit for wireless communication. The wireless communications circuit 550 within integrated circuit 440 is connected to an antenna 560. In other embodiments, there may be a separate integrated circuit comprising communications circuit 550; moreover, there may be one or more further integrated circuit, and there may be other components such as transistors or passive devices such as resistors or capacitors, or even batteries. The components may be discrete or integrated, and may be formed as tracks or regions in or on the flexfoil or other substrate. In other embodiments, the integrated circuit includes a wired connection to an external device. The device may be a reader, a hand-held device such as a mobile phone, or some other electronic device such as a computer. Thus, in some embodiments, the test results may be read directly from the lateral flow test apparatus by a display such as without limitation an LCD (liquid crystal display), whereas in other embodiments, the test results—or even the raw data or intermediate data—may be transferred to another device for display, or further analysis, or even onwards transmission for, for instance data aggregation or further analysis or archiving.

Figure 6:
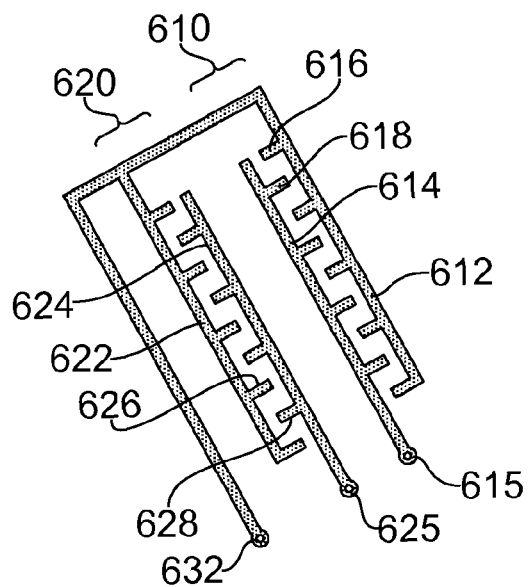
FIG. 6 shows an example of an electrode configuration for sensing and reference capacitors.

FIG. 6 shows an example of an electrode configuration for sensing and reference capacitors. The example configuration shown has a first capacitor 610 which operates as a sensing capacitor and a second capacitor 620 which operates as a reference capacitor. The pairs of capacitors 610 and 620 may form a test pair or a control pair, depending on their position relative to the test lines or test regions on the test strip. For definiteness, they will be termed hereinunder as sensing test capacitor 610 and a reference test capacitor 620, also it will be appreciated that they could also be termed as sensing control capacitor 610 (or 610') and reference control capacitor 620 (or 620'). As shown, the capacitors may have a first conductive plate, 612 and 622 respectively, which is connected to a common contact 632. The second conductive plate of each capacitor, 614 and 624 respectively, may be connected to separate respective contacts 615 and 625. As has already been discussed, the conductive plates, or electrodes, may take the form of printed metal tracks on or in a flexfoil, or metal tracks on a printed circuit board. In this case, it is particularly convenient if the conductive plates include interdigitated fingers 616, 618, and 626, 628 as shown, in order to increase the capacitance by reducing the average gap between the conductive plates and/or increasing the surface area of the capacitor conductive plates. As will be immediately familiar to the skilled person in the field of capacitance measurements, in use, an excitation signal may be supplied to common contact 632, and the resulting voltages present at contacts 615 and 625 measured and compared in order to measure a capacitance difference between the pair of capacitors.

Changes in the dielectric of the material in the vicinity of the conductive plates, and in particular in the material in the test strip, affects the capacitance values. By suitably locating the sensing test capacitor 610 adjacent to the test region 52 of the test strip, such that the dielectric of the capacitor is influenced by the presence of marker molecules at the test region, and locating the reference test capacitor nearby but not so close to the test region as to be significantly affected by the presence of marker molecule, the pair of capacitors may be used, in particular by measuring a difference in capacitance between them, to detect the presence of mocha molecules at the test region. Typically the reference capacitor is separated from the test capacitor by 1 mm to 2 mm. It will be appreciated that the positioning of the reference test capacitor is, in theory, unconstrained; however, the capacitance differences are generally small, as will be described further hereinunder, and so in order to minimise stray capacitance is, it is appropriate to position the reference test capacitor nearby to the test capacitor. It is preferable that the reference capacitor be close to the sensing capacitor in order to limit the effects of inhomogeneity of the membrane, test liquid and so on. Further, the tracks will generally have better matched capacitances, and in particular manufacturing inhomogeneities in the manufacturing of the metal tracks will have a reduced effect.

It will be further appreciated, that the capacitor arrangement shown in FIG. 6 is an example only, and alternative arrangements also fall within the scope of the invention. In particular, in some arrangements the two conductive plates of the sensing capacitor and/or the reference capacitor are arranged on opposite sides of the test strip membrane. One convenient method to facilitate this is to partially cut the flexfoil so as to have several teeth, with a capacitor conductive plate being on each consecutive tooth, and to alternately interleave these above and below the membrane. In order to ensure that the conductive plates are not in direct contact with the membrane the fluid thereon, it may be convenient to imbed the conductive plates as tracks between polymeric layers in the flexfoil. Of course, it will be appreciated that, in order to ensure a good capacitive response, a thick insulator, or one with a high dielectric, should generally be avoided.

Figure 8:
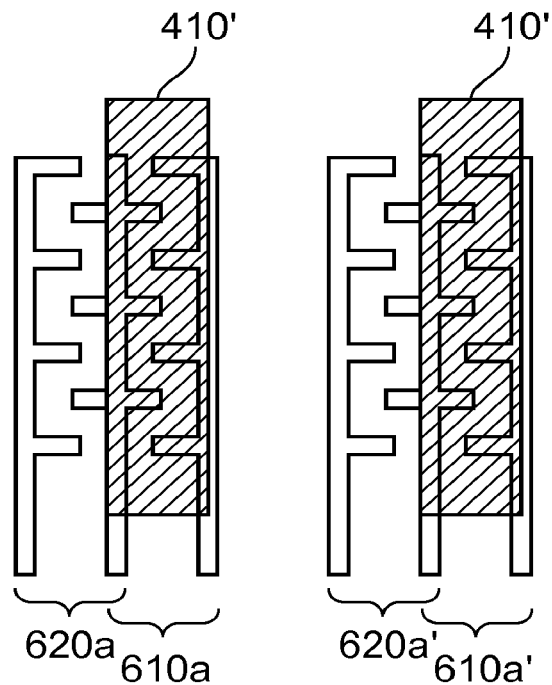
FIG. 8 shows an alternative arrangement of test and control pairs of capacitors.

FIG. 8 shows an alternative arrangement of test and control pairs of capacitors: similarly to the arrangement depicted in FIG. 6, the test pair of capacitors comprises a sensing capacitor 610*a*, and a reference capacitor 620*a*. The sensing capacitor 610*a* is exposed either directly or indirectly to the sample analyte, by means of the test strip, shown as 410'. In contrast to FIG. 6, in FIG. 8 the control pair of capacitors are explicitly shown; this pair is located further to the right of the figure, in which it is assumed that the flow is from left to right. The control pair of capacitors comprises a sensing control capacitor 610*a'* and a reference control capacitor 620*a'*.

Figure 9:
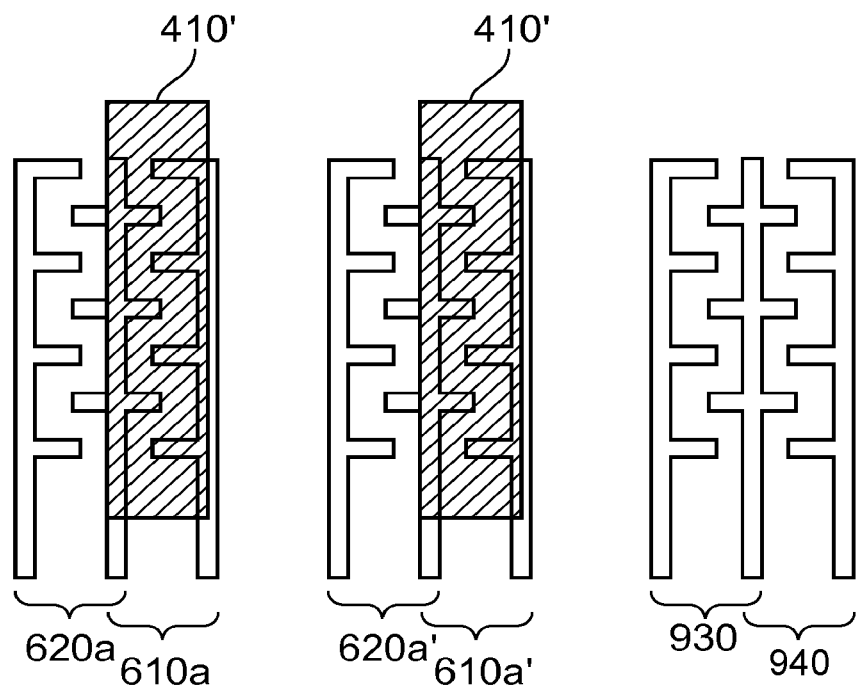
FIG. 9 shows a further arrangement of test and control pairs of capacitors, and including a pair of ambient capacitors.

FIG. 9 shows a further arrangement of test and control pairs of capacitors, and includes a further pair of capacitors which may be denoted ambient capacitors. This further pair of capacitors may be also considered as a reference pair of capacitors; hereinafter the term ambient capacitors will be used in to reduce any risk of confusion with the reference capacitors 620, 620', 620*a*, 620*a'*—which form part of the sensing and the control pairs of capacitors. The ambient capacitors comprise a further pair of capacitors 940 and 930. Although these capacitors are physically shown on the figure as being further to the right, their location may be suitably chosen in order to ensure they are not affected by the flow of the sample analyte. That is to say, neither of the capacitors come into contact either directly or indirectly with the test strip 410'.

In the arrangement shown in FIG. 9, the inclusion of the ambient pair of capacitors 930 and 940 results in a measurement system in which there is a pair of capacitors which should be entirely uninfluenced by the lateral flow of the sample analyte itself, or the measurements; that is to say this additional pair of capacitors may be used to monitor the ambient conditions. Post-processing of the measurements may then be applied, as will be familiar to the skilled person, in order to eliminate effects of such ambient conditions—due to for instance changes in humidity—resulting in a test which may be less sensitive to environmental or ambient conditions, and in particular may have an improved overall signal-to-noise ratio.

FIG. 7 shows, at FIG. 7(*a*) to FIG. 7(*f*) respectively, δC, which is the absolute difference between the capacitances of the sensing and reference capacitors, that is:

$$\delta C = |C_{sens} - C_{ref}|$$

for the test line and control line capacitors, at different moments during a lateral flow test. Along the top of each figure is a schematic section showing the path of the lateral flow test from sample pad 30 across conjugate pad 40, along the membrane 50, and across test line and control line 52 and 54 respectively, and, at the right-hand end, the absorbent pad 60. At any particular moment during the test corresponding to each of the figures, the distance to which the sample and light has diffused is shown by the top left to bottom right hashing. Underneath the membrane is a backing film 420 having capacitors embedded therein. As shown, the capacitors are sensing test capacitor 610, reference test capacitor 620, sensing control capacitor 610', and reference control capacitor 620'.

In each diagram, beneath the schematic are shown two curves. The upper curve is the capacitance difference ΔCt 710 between the sense test capacitor and the reference test capacitor, and the lower curve is the capacitance difference ΔCc 720 between the reference and sense control capacitor and the reference control capacitor.

FIG. 7(*a*) shows the situation when the sample analyte has reached the first (reference test) capacitor 620. Due to the presence of sample only in the vicinity of reference test capacitor 620, ΔCt 710 rises sharply at 711. This is because the sample fluid induces a significant change in the dielectric permittivity in the vicinity of the reference test capacitor 620. ΔCc 720 remains flat.

At FIG. 7(*b*), the sample analyte has reached the second (sense test) capacitor 610. The fluid is now present in the vicinity of both the reference test capacitor 620 and the sample test capacitor 610, so the capacitance difference between these two capacitors disappears, as shown the trace falls back to at 712. Since the sample analyte has not yet reached either of the control electrodes, ΔCc 720 remains flat.

FIG. 7(*c*), represents a later moment, but still before the front of the sample reaches the control capacitor. As more sample passes the test region 52, the bioreceptors thereat capture marker molecules which start to accumulate in this region. There is thus, as shown at 713, a gradual increase in the capacitance difference ΔCt 710.

At the moment represented by FIG. 7(*d*), the fluid front has reached and passed both the sense control capacitor and the reference control capacitor. The capacitance difference ΔCc 720 thus undergoes both the sharp rise at 721 and the sharp fall at 722 analogous to the sharp rise and fall at 711 and 12 respectively for the capacitance difference ΔCt, due to the arrival of the fluid affecting the permittivity in the vicinity of the first of the sense control cacpacitor 610', producing the sharp rise, and then the reference control cacpacitor 620' balancing this out to produce the sharp fall back to close to the original level capacitor. In practical devices, there is may be a non-zero offset between the sensing and reference capacitors, due for instance to manufacturing tolerances that is to say, ΔCt may not start at zero. This offset is generally magnified by the introduction of the fluid, that is to say ΔCt may not fall to zero at the end of the sharp fall, if even the original offset has been cancelled off. It may therefore be appropriate to "re-zero", or cancel this magnified offset, at the end of the steep fall, and just prior to commencing measuring of the accumulating molecules.

Finally, as shown in FIG. 7(*e*), as further fluid flows past both the test electrodes and the control electrodes, the bioreceptors thereat capture more marker molecules, so each of the signals 710 and the 720 rise (shown at 713 and 723 respectively). As shown the rise is slower than that due to the initial arrival of the fluid; the rise may also typically either be asymptotic as the bioreceptors become increasingly saturated, or, the rate of rise may decrease the sample flow rate decreases due to a reduced pressure differential between the sample pad and the absorbent pad.

In summary then, as shown in FIG. 7, the signal 710 can provide an indication regarding the presence (or absence) of the test molecule in the sample analyte. It will further be appreciated that the magnitude of the signal 730 can give an indication not only of the presence, but of the relative concentration of the test molecule.

However, it is also possible to use the measurements to provide an accurate estimate of the flow rate of the sample analyte. If the concentration of the bioreceptor is known, it may then be possible to deduce an absolute concentration of the test molecule in the sample analyte.

Since the spacing S between the test region and control the region may be well determined, the time difference T between the sharp rise in ΔCt at 711 and the sharp rise in ΔCc at 72 provides a direct indication of the velocity (S/T) of travel of the front of the sample. Then, provided that the cross-sectional area (A) and porosity (P) of the test sample are known or can be estimated with reasonable accuracy, the volume flow rate (VFR) of the sample analyte can be determined, through:

$$VFR = S \cdot A \cdot P / T$$

It will be appreciated that instead of the relative time of the rise of the two signals, the relative time of the rise and fall of one of the signals (that is to say either 711 and 712, or 721 and 722), may be used to estimate the volume flow rate. However due to the increased relative separation of the two pairs of capacitors compared with the relative closeness of the reference and sense capacitor at and near each of the test and control regions, the timing of the two sharp rises will generally provide a more accurate measurement. It will be appreciated that the timing of the sharp falls could be used with a similar level of accuracy to the sharp rises.

The capacitance difference δC, induced by the presence of molecules labelled with metallic label particles (e.g., nano gold particles) in the test region, may be estimated through:

$$\delta C \approx 3\Omega_P \varepsilon_E \int\int_\Omega \int_E \left( \frac{E(x, y, z)}{V} \right)^2 N_P(x, y, z) \, dx \, dy \, dz$$

where $\Omega_P$ is the volume of the label particle, $\in_E$ is the permittivity of the membrane (wet or dry, depending on the stage of the test sequence) in the absence of any label particles, Np is the volume density of the label particles (number of label particles per unit of volume) accumulated at the test region, E is the electric field in the membrane, and V the potential at the position of a label particle; and the integration is carried out across the membrane volume $\Omega_E$.

Typical values are: δC=0.94 fF, C=0.89 pF and δC/C=1e-3. It will thus be appreciated that by using accurate capacitance measuring techniques, it is possible to determine the presence of the nano particles by change in capacitance difference. However, it was also be appreciated that the measurements are sensitive to noise, and noise reduction techniques such as enclosing the measuring area in a Faraday cage, may be helpful in improving the signal-to-noise ratio and thus the reliability of the measurements.

From the analysis above, it will be appreciated, that embodiments rely on the change in capacitance due to the label particles. In known lateral flow tests the label is generally chosen for an optimal optical—that is to say—an electromagnetic effect; in contradistinction, in embodiments, the label particle may be chosen for optimal or strong electronic, and in particular capacitive, effect. Embodiments may thus enable the use of a wider selection of label particles than has been available in lateral flow tests heretofore.

Since the precise measurement conditions may not be known a priori, it may not be possible to predetermine an optimum measurement frequency in order to determine the capacitance of one or both of the sensing and reference capacitors, that is Csens or Cref. In particular, the sample analyte properties such as iron concentration or composition are unlikely to be precisely known. A higher signal-to-noise ratio (SNR) may be obtainable at one frequency compared to that obtainable at the different frequency. It may therefore be beneficial to measure the capacitance at more than one frequency. In example embodiments of the measurement frequency for the capacitance measurement is swept across a range of frequencies, in order to determine an optimum frequency, at which the test sensitivity is highest.

Example ranges of frequencies used for such a frequencies suite are 1 kHz to 10 GHz, and 10 kHz to 1 MHz. The sensing and reference test capacitors, may be swept through the range of frequencies independently, or at the same time. All of the measurements may be made using a range of frequencies, or the frequency may be swept during an initial measurement phase, and thereafter only the optimum frequency be used.

Similarly, in embodiments in which there are further, control, capacitors, the measurements of these may be made using the same frequency sweeping techniques.

In some embodiments, the signal to noise ratio for the capacitance measurements may be further enhanced by contacting the sample analyte to an electrical ground. Methods to do so will be immediately apparent to the skilled person. For example an electrical contact between the ground of the electronic circuit and is one of the lateral flow test components such as sample pad, conjured pad, or the membrane may be made. In one embodiment, an electrical contact is made to the sample pad 30.

From reading the present disclosure, other variations and modifications will be apparent to the skilled person. Such variations and modifications may involve equivalent and other features which are already known in the art of lateral flow tests, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination.

The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:

1. A lateral flow test arrangement for at least one test molecule comprising:
   a test strip for transporting an analyte having the at least one test molecule away from a sampling region and towards an absorbing reservoir region, the test strip having therein and remote from the sampling region, a test region for functionalization with a molecule which binds to the at least one test molecule or to a conjugate of the at least one test molecule;
   a sensing test capacitor in the test region, the sensing test capacitor having a dielectric material having a dielectric permittivity influenced by the presence of marker molecules, having a first pair of electrodes configured to measure a first capacitance, and extending across the test strip at least partially aligned with the test region;
   a reference test capacitor near the test region, having a second pair of electrodes configured to measure a second capacitance, and extending across the test strip; and
   an electronic circuit configured to measure a time-dependant capacitance difference between the capacitances of the sensing test capacitor and the reference test capacitor,
   wherein the test strip further includes a control region for functionalization with a second molecule different from the molecule in the test region, the lateral flow test arrangement further including a sensing control capacitor having a third pair of electrodes extending across the test strip at least partially aligned with the control region and extending across the test strip; and
   a reference control capacitor having a fourth pair of electrodes extending across the test strip,
   wherein the electronic circuit is further configured to measure a time-dependant capacitance difference between the sensing control capacitor and the reference control capacitor.

2. The lateral flow test arrangement according to claim 1, wherein at least one of: the first pair of electrodes of the sensing test capacitor are both on the same side of the test strip, and the second pair of electrodes of the reference test capacitor are both on the same side of the test strip.

3. The lateral flow test arrangement according to claim 1, wherein the first pair of electrodes of the sensing test capacitor and the second pair of electrodes of the reference test capacitor comprise conducting tracks in a substrate flex-foil, and the substrate flex-foil is arranged to provide electrical isolation between the first and second pair of electrodes and the test strip.

4. The lateral flow test arrangement according to claim 1, wherein the electronic circuit is further configured to measure the capacitance of at least one of the sensing test capacitor and the reference test capacitor at a plurality of frequencies.

5. The lateral flow test arrangement according to 4, wherein the electronic circuit is further configured to determine a volume flow rate from the time-dependant capacitance difference between the sensing control capacitor and the reference control capacitor and the time-dependant capacitance difference between the capacitance of the sensing test capacitor and the capacitance of the reference test capacitor.

6. The lateral flow test arrangement according to claim 1, further comprising a data display for displaying data from the electronic circuit.

7. The lateral flow test arrangement according to claim 1, further comprising communication circuit for communicating data from the electronic circuit to an external device.

8. The lateral flow test arrangement according to claim 1, the test strip having there across and remote from the sampling region, a further test line for functionalization with a further molecule which binds to the further at least one test molecule; the lateral flow test arrangement test further comprising:
   a further sensing test capacitor having a fifth pair of electrodes longitudinally aligned with the test line and extending across the test strip;
   a further reference test capacitor having a sixth pair of electrodes extending across the test strip,
   wherein the electronic circuit is further configured to measure a time-dependant capacitance difference between the further sensing test capacitor and the further reference test capacitor.

9. The lateral flow test arrangement according to claim 1, wherein the lateral flow test arrangement is configured to monitor a concentration of a target molecule or molecules of the at least one molecule in the analyte.

10. The lateral flow test arrangement according to claim 8, wherein the lateral flow test arrangement is configured to monitor a concentration of a plurality of different target molecules in the analyte.

11. The lateral flow test arrangement according to claim 9, wherein the target molecule or molecules may be is a respective one of or a plurality of molecules from the set consisting of DNA, proteins, enzymes, peptides, cells, bacteria, small molecules and hormones.

12. The lateral flow test arrangement according to claim 1, wherein the first pair of electrodes includes conductive plates with interdigitated fingers to increase the capacitance between the conductive plates.

13. The lateral flow test arrangement according to claim 1, wherein the second pair of electrodes includes conductive plates with interdigitated fingers to increase the surface area of the conductive plates.

14. The lateral flow test arrangement according to claim 1, wherein the reference test capacitor is not significantly affected by the presence of the marker molecules in the test region.

15. A pregnancy test system including a lateral flow test arrangement for at least one test molecule comprising:
- a test strip for transporting an analyte having the at least one test molecule away from a sampling region and towards an absorbing reservoir region, the test strip having therein and remote from the sampling region, a test region for functionalization with a molecule which binds to the at least one test molecule or to a conjugate of the at least one test molecule;
- a sensing test capacitor in the test region, the sensing test capacitor having a dielectric material having a dielectric permittivity influenced by the presence of marker molecules, having a first pair of electrodes configured to measure a first capacitance, and extending across the test strip at least partially aligned with the test region;
- a reference test capacitor near the test region, having a second pair of electrodes configured to measure a second capacitance, and extending across the test strip; and
- an electronic circuit configured to measure a time-dependant capacitance difference between the capacitances of the sensing test capacitor and the reference test capacitor,
wherein the test strip further includes a control region for functionalization with a second molecule different from the molecule in the test region, the lateral flow test arrangement further including a sensing control capacitor having a third pair of electrodes extending across the test strip at least partially aligned with the control region and extending across the test strip; and
- a reference control capacitor having a fourth pair of electrodes extending across the test strip,
wherein the electronic circuit is further configured to measure a time-dependant capacitance difference between the sensing control capacitor and the reference control capacitor.

* * * * *